United States Patent
Dang et al.

(10) Patent No.: US 9,932,318 B2
(45) Date of Patent: Apr. 3, 2018

(54) CATALYST PERFORMANCE IN PROPYLENE EPOXIDATION

(71) Applicant: Lyondell Chemical Technology, L.P., Houston, TX (US)

(72) Inventors: Vu A. Dang, Bear, DE (US); David W. Leyshon, Houston, TX (US); Sandor Nagy, Seabrook, TX (US); Roger A. Grey, West Chester, PA (US)

(73) Assignee: Lyondell Chemical Technology, L.P., Houston, TX (US)

( * ) Notice: Subject to any disclaimer, the term of this patent is extended or adjusted under 35 U.S.C. 154(b) by 0 days.

(21) Appl. No.: 15/093,270

(22) Filed: Apr. 7, 2016

(65) Prior Publication Data
US 2016/0297782 A1   Oct. 13, 2016

Related U.S. Application Data

(60) Provisional application No. 62/145,313, filed on Apr. 9, 2015.

(51) Int. Cl.
*C07D 301/12* (2006.01)
*B01J 29/89* (2006.01)

(52) U.S. Cl.
CPC ............ *C07D 301/12* (2013.01); *B01J 29/89* (2013.01)

(58) Field of Classification Search
CPC .................................................. B01J 2231/72
See application file for complete search history.

(56) References Cited

U.S. PATENT DOCUMENTS

| | | | |
|---|---|---|---|
| 5,591,875 A | 1/1997 | Chang et al. | |
| 6,429,323 B1 | 8/2002 | Escrig et al. | |
| 6,441,204 B1 | 8/2002 | Grey | |
| 8,124,555 B2 * | 2/2012 | Mandimutsira | B01J 29/89 502/107 |
| 2011/0152550 A1 | 6/2011 | Grey et al. | |
| 2011/0190517 A1 | 8/2011 | Mandimutsira et al. | |
| 2016/0185741 A1 | 6/2016 | Teles et al. | |

FOREIGN PATENT DOCUMENTS

| | | |
|---|---|---|
| EP | 757045 A1 | 2/1997 |
| EP | 1074548 A1 | 2/2001 |
| WO | WO-03/035630 A1 | 5/2003 |
| WO | WO-2011075302 A1 | 6/2011 |
| WO | WO-2012018408 A2 | 2/2012 |
| WO | WO-2015010992 A1 | 1/2015 |

OTHER PUBLICATIONS

PCT/US2016/026443 International Search Report and Written Opinion dated Jun. 27, 2016.

* cited by examiner

*Primary Examiner* — Heidi Reese

(57) ABSTRACT

The present disclosure relates to a method of epoxidizing an olefin to form an epoxide, the method comprising contacting an alkene$_{(C\leq12)}$ or aralkene$_{(C\leq12)}$ with a titanium silica catalyst, a peroxide, a buffer, and one or more organic solvents in a reaction mixture, wherein the one or more organic solvents comprise a first organic solvent selected from:

$$R_1\text{—OH} \quad (I),$$
$$R_2\text{—CN} \quad (II),$$
$$R_3\text{—C(O)—}R_4 \quad (III) \text{ or}$$
$$R_5\text{—O—}R_6 \quad (IV)$$

wherein:
$R_1$ is alkyl$_{(C\leq12)}$, aryl$_{(C\leq12)}$, aralkyl$_{(C\leq12)}$ or a substituted version of any of these groups;
$R_2$ is alkyl$_{(C\leq12)}$, aryl$_{(C\leq12)}$, aralkyl$_{(C\leq12)}$ or a substituted version of any of these groups;
$R_3$ is hydrogen, alkyl$_{(C\leq6)}$ or substituted alkyl$_{(C\leq6)}$; and
$R_4$, $R_5$, and $R_6$ are each independently selected from alkyl$_{(C\leq12)}$, aryl$_{(C\leq12)}$, aralkyl$_{(C\leq12)}$ or a substituted version of any of these groups, or are taken together are alkoxydiyl$_{(C\leq12)}$, alkanediyl$_{(C\leq12)}$, substituted alkoxydiyl$_{(C\leq12)}$ or substituted alkanediyl$_{(C\leq12)}$.

14 Claims, 1 Drawing Sheet

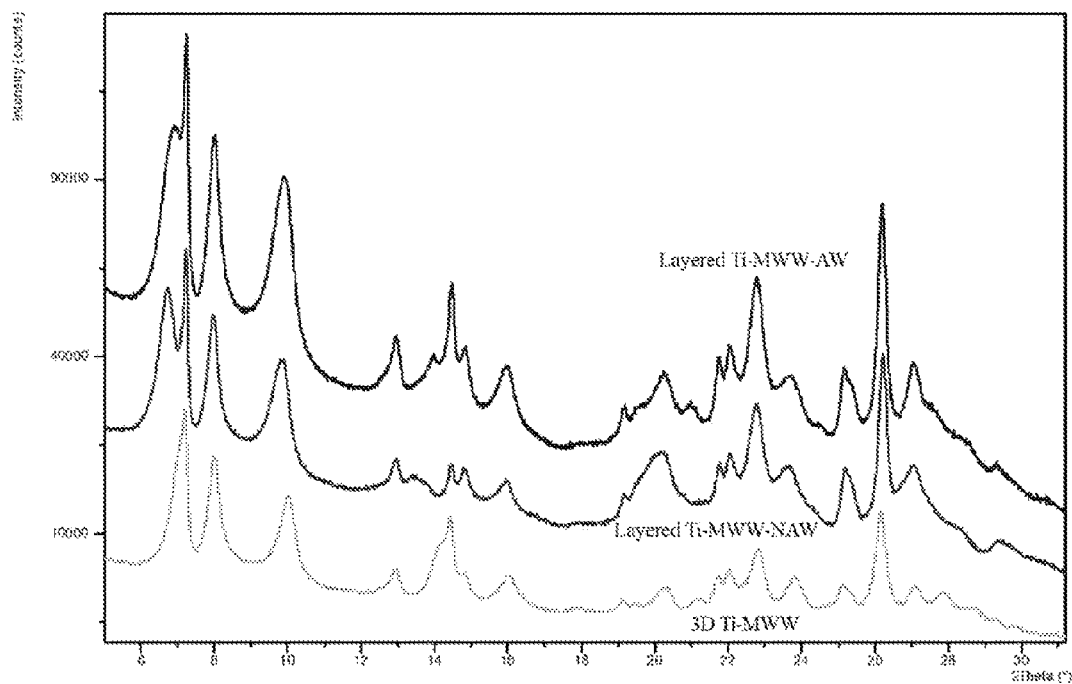

CATALYST PERFORMANCE IN PROPYLENE EPOXIDATION

CROSS-REFERENCE TO RELATED APPLICATIONS

This application claims the benefit of priority to U.S. Provisional Application No. 62/145,313, filed on Apr. 9, 2015, which is incorporated herein by reference in its entirety.

BACKGROUND OF THE INVENTION

I. Technical Field

The present disclosure relates to the production of epoxidation products form alkenes. Specifically, the present disclosure relates to the use of buffers and large molecule solvents to improve the catalytic efficacy of a titanium silica catalyst in the epoxidations of alkene and aralkenes.

II. Description of Related Art

Many methods for the preparation of epoxides have been developed including the epoxidation of an olefin with an oxidizing agent in the presence of a catalyst and the direct epoxidation of an olefin with oxygen in the presence of a catalyst. Some oxidizing agents which are useful in the epoxidation of an olefin include organic hydroperoxide including 1-phenylethyl hydroperoxide and tert-butyl hydroperoxide. Use of these and similar oxidizing agents in commercial epoxidation process are described in U.S. Pat. Nos. 3,351,635 and 4,367,342. Hydrogen peroxide can also be used as an oxidizing agent for the epoxidation of olefins with a titanium catalyst as described in U.S. Pat. No. 4,833,260. Furthermore, titanium silica catalysts are used in conjunction with a noble metal catalyst such as a Group VII metal, e.g. palladium, to lead to direct epoxidation of an olefin with oxygen as described in JP Pat. Doc. 4-352771.

Titanium silicate catalysts, TS-1, which are used commercially by Dow and BASF to produce propylene oxide, can be efficient catalysts for the epoxidation reaction, but they require methanol to be effective. Since methanol is a small molecule, it can react with propylene oxide to yield undesirable ring opening byproducts such as 1-methoxy-2-propanol or 2-methoxy-1-propanol. In addition, water, which is also used as a co-solvent in most cases, will react with propylene oxide to yield propylene glycol as a byproduct. In both situations, propylene oxide yield will be reduced because of the ring opening side reactions taken place. The addition of buffers helps reduce the amount of ring opened products formed but also significantly reduces the catalytic performance. As such, the identification of a catalytic system which allows for the use of buffer and/or a wider range of solvents while maintaining high catalytic efficacy and low amounts of ring opened byproducts is of commercial interest.

SUMMARY OF THE INVENTION

In one aspect of the present disclosure, there are provided improved methods for the epoxidation of alkenes and aralkenes. Additionally, the present disclosure provides methods of using a titanium silica catalyst in the present of a buffer and a large molecule solvent to produce a highly active catalytic complex to produce epoxides.

In some aspects, the present disclosure provides a method of epoxidizing an olefin to form an epoxide, the method comprising contacting an alkene$_{(C \leq 12)}$ or aralkene$_{(C \leq 12)}$ in a reaction mixture comprising a titanium silica catalyst, a peroxide, a buffer, and one or more organic solvents, wherein the one or more organic solvents comprise a first organic solvent selected from:

$R_1$—OH    (I),

$R_2$—CN    (II),

$R_3$—C(O)—$R_4$    (III), or

$R_5$—O—$R_6$    (IV)

wherein $R_1$ is alkyl$_{(C \leq 12)}$, aryl$_{(C \leq 12)}$, aralkyl$_{(C \leq 12)}$, or a substituted version of any of these groups; $R_2$ is alkyl$_{(C \leq 12)}$, aryl$_{(C \leq 12)}$, aralkyl$_{(C \leq 12)}$, or a substituted version of any of these groups; $R_3$ is hydrogen, alkyl$_{(C \leq 6)}$, or substituted alkyl$_{(C \leq 6)}$; and $R_4$, $R_5$, and $R_6$ are each independently selected from alkyl$_{(C \leq 12)}$, aryl$_{(C \leq 12)}$, aralkyl$_{(C \leq 12)}$, or a substituted version of any of these groups, or are taken together are alkoxydiyl$_{(C \leq 12)}$, alkanediyl$_{(C \leq 12)}$, substituted alkoxydiyl$_{(C \leq 12)}$ or substituted alkanediyl$_{(C \leq 12)}$. In certain embodiments, the first organic solvents further comprise from about 0.1% to about 50% water by weight based upon the total weight of the first organic solvent. In further embodiments, the first organic solvent comprises from about 0.1% to about 40% water by weight based upon the total weight of the first organic solvent. In certain embodiments, the first organic solvent comprises from about 0.1% to 30% water by weight based upon the total weight of the first organic solvent. In some embodiments, the first organic solvent is selected from acetophenone, 1-phenylethyl alcohol, acetonitrile, glyme, dimethyl ethylene glycol ether, tert-butyl alcohol, trioxane, dioxane, isopropyl alcohol, acetone, cyclohexanone and acetophenone. In some embodiments, the one or more organic solvents further comprise a second organic solvent selected from:

$R_1$—OH    (I),

$R_2$—CN    (II),

$R_3$—C(O)—$R_4$    (III), or

$R_5$—O—$R_6$    (IV)

wherein $R_1$ is alkyl$_{(C \leq 12)}$, aryl$_{(C \leq 12)}$, aralkyl$_{(C \leq 12)}$, or a substituted version of any of these groups; $R_2$ is alkyl$_{(C \leq 12)}$, aryl$_{(C \leq 12)}$, aralkyl$_{(C \leq 12)}$, or a substituted version of any of these groups; $R_3$ is hydrogen, alkyl$_{(C \leq 6)}$, or substituted alkyl$_{(C \leq 6)}$; and $R_4$, $R_5$, and $R_6$ are each independently selected from alkyl$_{(C \leq 12)}$, aryl$_{(C \leq 12)}$, aralkyl$_{(C \leq 12)}$, or a substituted version of any of these groups, or are taken together are alkoxydiyl$_{(C \leq 12)}$, alkanediyl$_{(C \leq 12)}$, substituted alkoxydiyl$_{(C \leq 12)}$ or substituted alkanediyl$_{(C \leq 12)}$. In certain embodiments, $R_1$ is alkyl$_{(C4-6)}$. In some embodiments, $R_1$ is tert-butyl. In further embodiments, $R_1$ is aralkyl$_{(C \leq 12)}$. In some embodiments, $R_1$ 1-phenylethyl. In certain embodiments, $R_2$ is alkyl$_{(C \leq 6)}$. In further embodiments, $R_2$ is methyl. In some embodiments, $R_3$ is alkyl$_{(C \leq 6)}$. In additional embodiments, $R_3$ is methyl. In certain embodiments, $R_4$ is aryl$_{(C \leq 8)}$. In some embodiments, $R_4$ is phenyl. In further embodiments, the first organic solvent is 1-phenylethyl alcohol and the second organic solvent is acetophenone. In additional embodiments, the reaction mixture comprises a weight ratio of acetophenone to 1-phenylethyl alcohol of 1 part acetophenone to 99 parts 1-phenylethyl alcohol to 50 parts acetophenone to 50 parts 1-phenylethyl alcohol. In some embodiments, the weight ratio of acetophenone to 1-phenylethyl alcohol is 8 to 92. In certain embodiments, the first organic solvent is acetonitrile. In additional embodiments, the first organic solvent is tert-butyl alcohol. In some embodiments, the first organic solvent is 1-phenylethyl alcohol. In some embodiments, the peroxide is hydrogen peroxide, tert-butyl hydroperoxide, 1-phenylethyl hydroperoxide or cumyl hydroperoxide. In some embodiments, the peroxide is hydrogen peroxide. In further embodiments, the reaction mixture comprises a ratio of alkene$_{(C\leq12)}$ or aralkene$_{(C\leq12)}$ to the peroxide of greater than 1 to 5. In certain embodiments, the ratio of alkene$_{(C\leq12)}$ or aralkene$_{(C\leq12)}$ to the peroxide is greater than 3 to 1. In some embodiments, the ratio of alkene$_{(C\leq12)}$ or aralkene$_{(C\leq12)}$ to the peroxide is greater than 10 to 1. In additional embodiments, the titanium silica catalyst comprises a silica zeolite catalyst which comprises a silica framework in which silicon atoms in the silica framework have been replaced with titanium atoms. In further embodiments, the zeolite is an aluminosilicate MWW zeolite. In some embodiments, the ratio of titanium to silica in the titanium silica catalyst comprises a ratio of 0.5 to 14 titanium atoms for every 100 silicon atoms. In further embodiments, the method further comprises washing the titanium silica catalyst with a templating agent. In additional embodiments, the templating agent is a base. In some embodiments, the templating agent is piperidine, hexamethyleneimine, adamantyl ammonium hydroxide, octyltrimethylammonium hydroxide, hetyltrimethylammonium hydroxide, hexyltrimethylammonium hydroxide, hexyltrimethylammonium hydroxide or trimethyladamantylammonium hydroxide. In further embodiments, the method further comprises washing the catalyst with an acid after washing with a templating agent. In additional embodiments, the acid is nitric acid, hydrochloric acid, sulfuric acid, sulfurous acid, phosphoric acid or ammonium chloride. In some embodiments, the titanium silica catalyst is calcined at a temperature from about 400° C. to about 800° C. In further embodiments, the buffer is selected from a buffer of the formula:

$$X_1^+X_2^- \qquad (V)$$

wherein $X_1^+$ is selected from a Group 1 cation, Group 2 cation, ammonium, tetraalkylammonium$_{(C\leq24)}$, tetraarylammonium$_{(C\leq32)}$, tetraaralkylammonium$_{(C\leq36)}$, substituted tetraalkylammonium$_{(C\leq20)}$, substituted tetraarylammonium$_{(C\leq32)}$, substituted tetraaralkylammonium$_{(C\leq36)}$ or heteroarenium$_{(C\leq18)}$, and; $X_2^-$ is selected from alkylcarboxylate$_{(C\leq12)}$, alkenylcarboxylate$_{(C\leq12)}$, alkynylcarboxylate$_{(C\leq12)}$, arylcarboxylate$_{(C\leq12)}$, aralkylcarboxylate$_{(C\leq12)}$, heteroarylcarboxylate$_{(C\leq12)}$, heterocycloalkylcarboxylate$_{(C\leq12)}$, phosphate, hydroxide, silicate, aluminosilicate or sulfate. In some embodiments, $X_1^+$ is selected from a ammonium, tetraalkylammonium$_{(C\leq24)}$, tetraarylammonium$_{(C\leq32)}$, tetraaralkylammonium$_{(C\leq36)}$, substituted tetraalkylammonium$_{(C\leq20)}$, substituted tetraarylammonium$_{(C\leq32)}$, substituted tetraaralkylammonium$_{(C\leq36)}$ or heteroarium$_{(C\leq18)}$. In further embodiments, $X_1^+$ is ammonium or tetraalkylammonium$_{(C\leq16)}$. In additional embodiments, $X_1^+$ is ammonium. In some embodiments, $X_2^-$ is alkylcarboxylate$_{(C\leq8)}$. In certain embodiments, $X_2^-$ is acetate. In further embodiments, $X_2^-$ is phosphate. In additional embodiments, $X_2^-$ is dihydrogen phosphate. In some embodiments, the buffer is ammonium acetate or ammonium dihydrogen phosphate. In certain embodiments, the alkene$_{(C\leq12)}$ is propylene or 1-octene. In further embodiments, the alkene$_{(C\leq12)}$ is propylene. In additional embodiments, the method comprises heating the reaction mixture to a temperature is from about 20° C. to about 250° C., such as from about 20 to about 150° C. In some embodiments, the method comprises a pressure from about 10 psig (about 170 kPa) to about 1000 psig (about 7000 kPa). In some embodiments, the method comprises a pressure from about 50 psig (about 446 kPa) to about 1000 psig (about 7000 kPa). In some embodiments, the pressure is from about 100 psig (about 790 kPa) to about 500 psig (about 3500 kPa). In some embodiments, the pressure is about 300 psig (about 2,170 kPa). In some embodiments, the titanium silica catalyst comprises titanium impregnated on the MWW zeolite and the buffer is a buffer of the formula:

$$X_1^+X_2^- \qquad (V)$$

wherein: $X_1^+$ is selected from a Group 1 cation, Group 2 cation, ammonium, tetraalkylammonium$_{(C\leq24)}$, tetraarylammonium$_{(C\leq32)}$, tetraaralkylammonium$_{(C\leq36)}$, substituted tetraalkylammonium$_{(C\leq20)}$, substituted tetraarylammonium$_{(C\leq32)}$, or substituted tetraaralkylammonium$_{(C\leq36)}$, pyridinium and; $X_2^-$ is selected from alkylcarboxylate$_{(C\leq12)}$, alkenylcarboxylate$_{(C\leq12)}$, alkynylcarboxylate$_{(C\leq12)}$, arylcarboxylate$_{(C\leq12)}$, aralkylcarboxylate$_{(C\leq12)}$, heteroarylcarboxylate$_{(C\leq12)}$, heterocycloalkylcarboxylate$_{(C\leq12)}$, phosphate, hydroxide, silicate, aluminosilicate or sulfate. In certain embodiments, the titanium silica catalyst is treated with a templating agent. In further embodiments, the templating agent is piperidine. In some embodiments, the titanium silica catalyst is washed with an acid. In additional embodiments, the acid is nitric acid, hydrochloric acid, sulfuric acid, sulfurous acid, phosphoric acid or ammonium chloride. In some embodiments, the organic solvent further comprises from about 1% to about 40% water, such as from about 1% to about 10% water and about 8% water. In other embodiments, the organic solvent comprises from about 25% to about 35% water, such as about 30% water. In some embodiments, the organic solvent is t-butyl alcohol. In other embodiments, the organic solvent is 1-phenylethyl alcohol. In further embodiments, the organic solvent is 1-phenylethyl alcohol and acetophenone. In additional embodiments, the reaction mixture comprises a ratio of 1-phenylethyl alcohol to acetophenone to hydrogen peroxide to water from about 96:1:2.9:0.1 to 44:44:11.7:0.3. In some embodiments, the ratio of 1-phenylethyl alcohol to acetophenone to hydrogen peroxide to water is 76:18.9:5:0.1 to about 54:36:9.7:0.3. In further embodiments, the ratio of 1-phenylethyl alcohol to acetophenone to hydrogen peroxide to water is about 64:29:6.3:0.7. In additional embodiments, the titanium silica catalyst comprises titanium impregnated on the MWW zeolite and the organic solvent is 1-phenylethyl alcohol and acetophenone. In some embodiments, the titanium silica catalyst is treated with a templating agent. In further embodiments, the templating agent is piperidine. In some embodiments, the titanium silica catalyst is washed with a templating agent and then washed with an acid. In additional embodiments, the acid is nitric acid, hydrochloric acid, sulfuric acid, sulfurous acid, phosphoric acid or ammonium chloride. In further embodiments, the method further comprises reacting the alkene$_{(C\leq12)}$ or aralkene$_{(C\leq12)}$ with the titanium silica catalyst for a time period between about 1 minute and about 6 hours, such as about 30 minutes. In some embodiments, the method has a peroxide conversion percentage of greater than 10%, such as greater than 40% and greater than 90%. In certain embodiments, the method has a peroxide selectivity to the epoxide of greater than 40%, including greater than 50% and greater than 90%. In additional embodiments, the method has ring opening byproducts of the epoxidation that are less than 5% by weight of the epoxide produced by the method, such as less than 1% by weight of the epoxide produced by the method.

In yet another aspect, the present disclosure provides a method of epoxidizing an olefin to form an epoxide comprising:

a) adding an alkene$_{(C \leq 12)}$ or aralkene$_{(C \leq 12)}$ to a reaction vessel;
b) admixing a titanium silica catalyst, peroxide, buffer, and one or more organic solvents to the reaction vessel; and
c) contacting the alkene$_{(C \leq 12)}$ or aralkene$_{(C \leq 12)}$ with a catalyst in a reaction vessel.

In some embodiments, step a) and step b) are performed in any order. In further embodiments, the organic solvent further comprises from about 1% to about 40% water, including from about 1% to about 10% water and about 8% water. In additional embodiments, the organic solvent comprises from about 25% to about 35% water, including about 30% water. In some embodiments, the organic solvent further comprises one or more organic solvents selected from:

$$R_1 \text{—OH} \quad (I),$$

$$R_2 \text{—CN} \quad (II),$$

$$R_3 \text{—C(O)—} R_4 \quad (III), \text{ or}$$

$$R_5 \text{—O—} R_6 \quad (IV)$$

wherein: $R_1$ is alkyl$_{(C \leq 12)}$, aryl$_{(C \leq 12)}$, aralkyl$_{(C \leq 12)}$ or a substituted version of any of these groups; $R_2$ is alkyl$_{(C \leq 12)}$, aryl$_{(C \leq 12)}$, aralkyl$_{(C \leq 12)}$ or a substituted version of any of these groups; $R_3$ is hydrogen, alkyl$_{(C \leq 6)}$ or substituted alkyl$_{(C \leq 6)}$; and $R_4$, $R_5$ and $R_6$ are each independently selected from alkyl$_{(C \leq 12)}$, aryl$_{(C \leq 12)}$, aralkyl$_{(C \leq 12)}$ or a substituted version of any of these groups, or as taken together are alkoxydiyl$_{(C \leq 12)}$, alkanediyl$_{(C \leq 12)}$, substituted alkoxydiyl$_{(C \leq 12)}$ or substituted alkanediyl$_{(C \leq 12)}$. In further embodiments, $R_1$ is alkyl$_{(C4-6)}$. In some embodiments, $R_1$ is tert-butyl. In other embodiments, $R_1$ is aralkyl$_{(C \leq 12)}$. In additional embodiments, $R_1$ is 1-phenylethyl. In some embodiments, $R_2$ is alkyl$_{(C \leq 6)}$. In certain embodiments, $R_2$ is methyl. In further embodiments, $R_3$ is alkyl$_{(C \leq 6)}$. In some embodiments, $R_3$ is methyl. In certain embodiments, $R_4$ is aryl$_{(C \leq 8)}$. In additional embodiments, $R_4$ is phenyl. In some embodiments, the organic solvent is selected from acetophenone, 1-phenylethyl alcohol, acetonitrile or tert-butyl alcohol. In certain embodiments, a first organic solvent is 1-phenylethyl alcohol and a second organic solvent is acetophenone. In additional embodiments, the one or more organic solvent comprises a ratio of acetophenone and 1-phenylethyl alcohol of 8 to 92. In some embodiments, the organic solvent comprises acetonitrile. In other embodiments, the organic solvent comprises tert-butyl alcohol. In additional embodiments, the organic solvent comprises 1-phenylethyl alcohol. In further embodiments, the peroxide is hydrogen peroxide, tert-butyl hydroperoxide, 1-phenylethyl hydroperoxide or cumyl hydroperoxide. In some embodiments, the peroxide is hydrogen peroxide. In certain embodiments, the reaction vessel comprises a ratio of alkene$_{(C \leq 12)}$ or aralkene$_{(C \leq 12)}$ to the peroxide is greater than 1 to 5, such as greater than 3 to 1. In additional embodiments, the ratio of alkene$_{(C \leq 12)}$ or aralkene$_{(C \leq 12)}$ to the peroxide is greater than 10 to 1. In some embodiments, the titanium silica catalyst comprises a silica zeolite catalyst which comprises a silica framework in which silicon atoms in the silica framework have been replaced with titanium atoms. In certain embodiments, the silica zeolite is an aluminosilicate MWW zeolite. In further embodiments, the titanium silica catalyst comprises a ratio of 0.5 to 14 titanium atoms for every 100 silicon atoms. In some embodiments, the method further comprises washing the titanium silica catalyst with a templating agent. In some embodiments, the templating agent is a base. In some embodiments, the templating agent is piperidine, hexamethyleneimine, adamantyl ammonium hydroxide, octyltrimethylammonium hydroxide, hetyltrimethylammonium hydroxide, hexyltrimethylammonium hydroxide, hexyltrimethylammonium hydroxide, or trimethyladamantylammonium hydroxide. In certain embodiments, the method further comprises washing the catalyst with an acid after washing with a templating agent. In additional embodiments, the acid is nitric acid, hydrochloric acid, sulfuric acid, sulfurous acid, phosphoric acid, or ammonium chloride. In further embodiments, the titanium silica catalyst is calcined at a temperature from about 400° C. to about 800° C. In some embodiments, the buffer is selected from a buffer of the formula:

$$X_1^+ X_2^- \quad (IV)$$

wherein $X_1^+$ is selected from a Group 1 cation, Group 2 cation, ammonium, tetraalkylammonium$_{(C \leq 24)}$, tetraarylammonium$_{(C \leq 32)}$, tetraaralkylammonium$_{(C \leq 36)}$, substituted tetraalkylammonium$_{(C \leq 20)}$, substituted tetraarylammonium$_{(C \leq 32)}$, substituted tetraaralkylammonium$_{(C \leq 36)}$ or heteroarenium$_{(C \leq 18)}$; and $X_2^-$ is selected from alkylcarboxylate$_{(C \leq 12)}$, alkenylcarboxylate$_{(C \leq 12)}$, alkynylcarboxylate$_{(C \leq 12)}$, arylcarboxylate$_{(C \leq 12)}$, aralkylcarboxylate$_{(C \leq 12)}$, heteroarylcarboxylate$_{(C \leq 12)}$, heterocycloalkylcarboxylate$_{(C \leq 12)}$, phosphate or sulfate. In further embodiments, $X_1^+$ is ammonium or tetraalkylammonium$_{(C \leq 16)}$. In additional embodiments, $X_1^+$ is ammonium. In some embodiments, $X_2^-$ is alkylcarboxylate$_{(C \leq 8)}$. In certain embodiments, $X_2^-$ is acetate. In further embodiments, $X_2^-$ is phosphate. In additional embodiments, $X_2^-$ is dihydrogen phosphate. In some embodiments, the buffer is ammonium acetate or ammonium dihydrogen phosphate. In certain embodiments, the alkene$_{(C \leq 12)}$ is propylene or 1-octene. In additional embodiments, the alkene$_{(C \leq 12)}$ is propylene. In further embodiments, the method comprises heating the reaction vessel to a temperature between about 20° C. to about 250° C., such as from about 20° C. to about 150° C. and about 70° C. In certain embodiments, the method comprises a pressure from about 10 psig (about 170 kPa) to about 1000 psig (about 7000 kPa). In some embodiments, the method comprises a pressure from about 50 psig (about 446 kPa) to about 1000 psig (about 7000 kPa), including from about 100 psig (about 790 kPa) to about 500 psig (about 3500 kPa) and about 300 psig (about 2,170 kPa). In certain embodiments, the method further comprises reacting the alkene$_{(C \leq 12)}$ or aralkene$_{(C \leq 12)}$ with the titanium silica catalyst for a time period between about 1 minute to about 6 hours, such as about 30 minutes. In some embodiments, the method has a peroxide conversion percentage greater than 10%, including greater than 40% and greater than 90%. In additional embodiments, the method has a peroxide selectivity to the epoxide of greater than 40%, including greater than 50% and greater than 90%. In some embodiments, the method has ring opening byproducts of the epoxidation that are less than 5% by weight of the epoxide produced by the method, including less than 1% by weight of the epoxide produced by the method.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the appended claims will become apparent to those skilled in the art from this detailed description. Note that simply because a particular compound is ascribed to one particular generic formula does not mean that it cannot also belong to another generic formula.

BRIEF DESCRIPTION OF THE DRAWING

The FIGURE shows an XRD spectra of a TiMWW catalyst.

DETAILED DESCRIPTION OF THE INVENTION

I. Alkene and Aralkene Epoxidation Reaction

Carbon-carbon double bonds can react with hydrogen peroxide in the presence of a catalyst to form an epoxide. Such reactions can be used to generate an epoxide from a cis, trans, or terminal double bond. In some embodiments, the present disclosure utilizes an alkene$_{(C2-60)}$ for epoxidation. Additionally, an alkene with two or more double bonds may be used in the method described. In some embodiments, an alkene$_{(C3-20)}$ is utilized in the epoxidation reaction. In another embodiment, the alkene undergoing epoxidation is selected from propylene, butene, pentene, hexene, heptene, octene, nonene, decene, and their isomers. A broad number of conditions have been developed which can lead to an epoxide through the general reaction scheme shown below:

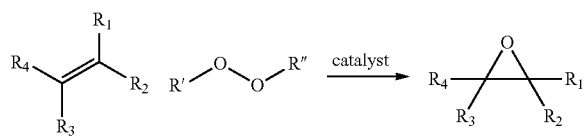

wherein R' and R" are each independently hydrogen, alkyl, substituted alkyl, aralkyl, substituted aralkyl, aryl or a substituted aryl. In some embodiments, R' and R" are each independently hydrogen, aralkyl, substituted aralkyl, alkyl or substituted alkyl. In certain embodiments, $R_1$, $R_2$, $R_3$, and $R_4$ are hydrogen, substituted or unsubstituted alkyl or substituted or unsubstituted aryl. In some embodiments, the alkyl group on $R_1$, $R_2$, $R_3$ or $R_4$ is a $C_2$-$C_{50}$ alkyl. In some embodiments, the alkyl group on $R_1$, $R_2$, $R_3$ or $R_4$ is $C_3$-$C_{20}$ alkyl. In other embodiments, the alkyl group on $R_1$, $R_2$, $R_3$, or $R_4$ is $C_3$-$C_{10}$ alkyl.

In some embodiments, a peroxide is used to lead to the epoxidation of the alkene. In certain embodiments, the peroxide is an organic peroxide wherein R' and/or R" is an alkyl or aralkyl group. In further embodiments, the alkyl or aralkyl groups have up to 50 carbons, including between 3 and 20 carbons. In certain embodiments, the organic peroxides that are used in the reaction of an alkene to form an epoxide include alkyl, cycloalkyl, aryl and aralkyl hydroperoxides. Examples include, but are not limited to, 1-phenylethyl hydroperoxide, tert-butyl hydroperoxide, tert-amyl hydroperoxide, cyclohexyl hydroperoxide and cumyl hydroperoxide. In additional embodiments, hydrogen peroxide (HOOH) can be used in the epoxidation reactions presented herein. The hydrogen peroxide may be generated prior to use in the epoxidation. In some embodiments, hydrogen peroxide is derived from any suitable source, including oxidation of secondary alcohol(s) such as isopropanol, from the anthraquinone process and from direct reaction of hydrogen and oxygen. Pre-formed hydrogen peroxide concentration ranges may be from 0.1 to 90% by weight of hydrogen peroxide in water, such as 1 to 10% by weight. The hydrogen peroxide may also be generated in situ by the reaction of hydrogen and oxygen in the presence of a noble metal catalyst. Although any sources of oxygen and hydrogen are suitable, in some embodiments, molecular oxygen and molecular hydrogen are utilized. In one embodiment of the present disclosure, the epoxidation of alkene with oxygen and hydrogen is carried out in the presence of a noble catalyst and the epoxidation catalyst described herein. In some embodiments, epoxidation is carried out in liquid (or supercritical or subcritical) phase. Suitable solvents include any chemical that is liquid under reaction conditions, including, but not limited to, oxygenated hydrocarbons such as alcohols like 1-phenylethyl alcohol, cyclohexanol, isopropanol and t-butyl alcohol; ethers such as dimethyl glycol ether; esters; ketones such as acetophenone, acetone and cyclohexanone; aromatic and aliphatic hydrocarbons such as toluene and hexane; nitriles such as acetonitrile; liquid $CO_2$ (in the supercritical or subcritical state) and water. In some embodiments, a fluorinated alcohol is used. In certain embodiments, solvents utilized in the epoxidation may include nitriles, alcohols, ketones or water. In some embodiments, the epoxidation comprises a mixture of solvents including mixtures of organic solvents and water. In further embodiments, the organic solvent is one or a mixture of the following: 1-phenylethyl alcohol, cyclohexanol, isopropyl alcohol, t-butyl alcohol, acetonitrile, glyme, dimethyl ethylene glycol ether, trioxane, dioxane, acetophenone, acetone or cyclohexanone.

In some aspects, a buffer may be useful for reducing the production of byproducts in the epoxidation reaction and/or increasing catalytic activity. In certain embodiments, the buffer may be any suitable salt(s) of the oxyacids, the nature and proportions of which in the mixture are such that the pH of their solution is in the range from about 3 to about 12, including from about 4 to about 10 and from about 5 to about 9. In some embodiments, suitable oxyacids contain an anion and a cation, wherein the anion is a phosphate, carbonate, bicarbonate, borate, hydroxide, silicate and aluminosilicate; and carboxylates such acetate, phthalate, oxylate, citrate or the like; the cation is an ammonium, alkylammonium, and protonated or alkylated N-heteroaryl groups such as tetraalkylammonium, pyridinium, N-methylpyridinium, and the like, alkali metals (Group 1 metal) or alkaline earth metals (Group 2 metal) or the like. Some non-limiting examples of the cation include $NH_4^+$, $NBu_4^+$, $NMe_4^+$, $Li^+$, $Na^+$, $K^+$, $Cs^+$, $Mg^{2+}$ and $Ca^{2+}$.

In some embodiments, buffers for use in the present technology contain more than one acceptable salt. In further embodiments, the concentration of the buffer is 0.1 mM to about 1 M, such as 0.5 mM to about 300 mM. In additional embodiments, ammonia gas or ammonium hydroxide may be added to the reaction mixture, which may be used to balance the pH of the reaction. Some non-limiting examples of buffers useful in the epoxidation reaction are alkali metal phosphate, ammonium dihydrogen phosphate, ammonium phosphate, ammonium hydroxide, ammonium acetate, ammonium benzoate, sodium acetate, sodium benzoate, sodium dihydrogen phosphate, potassium acetate, potassium benzoate or potassium dihydrogen phosphate.

In some embodiments, the catalyst contains a transition metal. The catalyst may be used to react with the carbon-carbon double bond to activate it towards attack with the peroxide or it may be used to facilitate the breakdown of the peroxide into a more reactive intermediate. The catalyst may also be used to increase the likelihood of the reaction of the formation of the desired epoxide product. In some embodiments, the catalyst used in the epoxidation reaction is a titanium catalyst. In further embodiments of the present disclosure, the titanium catalyst may contain other metals which further enhance the reactivity of the catalyst. In additional embodiments, the olefin to epoxidation catalyst is used at the minimum concentration of the catalyst necessary to affect the desired transformation with an appropriate yield and selectivity. In certain embodiments, the catalytically active titanium is present in a ratio to the peroxide of about 0.001 to about 100 mmoles of titanium per mole of peroxide, including about 0.01 to about 10 mmoles of titanium per mole of peroxide.

In some embodiments, the reaction of the oxidizing agent with the alkene is run with a molar ratio of alkene to oxidizing agent from about 1:100 to about 100:1, including from about 1:20 to about 20:1, about 1:5 to about 18:1, about 1:1 to about 15:1 and about 3:1 to about 10:1. Without being bound by theory, it is believed that at least one equivalent of oxidizing agent is needed to oxidize the alkene. While at least one equivalent of the oxidizing agent is needed to react with the alkene, in some embodiments, more than one equivalent of one of the materials is used to enhance the yield of the reaction. Additionally, the reaction is run under a pressure from about 20 to about 3000 pounds per square inch. In some embodiments, the pressure of the reaction is from about 50 to about 1000 pounds per square inch, from about 80 pounds per square inch to about 800 pounds per square inch and from about 100 pounds per square inch to 500 pounds per square inch. Additionally, in certain embodiments, the temperature of the reaction is modulated to improve yield or selectivity. In some embodiments, the temperature is from about ambient temperature to about 250° C., such as from about 20° C. to about 150° C., from about 20° C. to about 100° C. and from about 50° C. to about 80° C. In certain embodiments, the alcohol and ketone are present in a ratio of from no alcohol and about 100% ketone to about 100% alcohol and no ketone. Conversely, the ratio of hydrogen peroxide to water is from 0.1:99.9 to 90:10, including a ratio from 1:99 to 10:90. In some embodiments, the ratio of 1-phenylethyl alcohol to acetophenone to hydrogen peroxide to water from the oxidation in A is from 96:1:2.9:0.1 to 44:44:11.7:0.3. In some embodiments of the present disclosure, the ratio is from about 76:18.9:5:0.1 to about 54:36:9.7:0.3, such as about 64:29:6.3:0.7.

In some embodiments, a carrier gas is used. An appropriate carrier gas should be inert to the reaction conditions. Some non-limiting examples of carrier gases include helium, neon, argon, other noble gases, nitrogen, carbon dioxide or alkanes with between 1 and 8 carbon atoms. In certain embodiments, the carrier gases include nitrogen or an alkane with between 1 and 4 carbon atoms. In additional embodiments, the carrier gas comprises a mixture of two, three or more individual carrier gases. Furthermore, when the alkene is propylene and the carrier gas is propane, in certain embodiments, the addition of the carrier gas may be controlled and added at specific time points.

In some embodiments, the catalyst is a solid and represents a heterogeneous mixture with the alkene, the peroxide, the resultant epoxide and any solvents used to facilitate the reaction. In additional embodiments, the epoxidation reaction can be run on a commercial scale using a suitable reaction configuration including, but not limited to, continuous, batch, or semi-continuous configurations. Once the reaction has reached the desired level of completion, conventional methods of product recovery including, but not limited to, fractional distillation, selective extraction, filtration or other methods may be used to obtain the desired product. In some embodiments, recovered materials such as catalyst, reactor solvent, or unreacted olefin or peroxide can be recycled and reused.

The reaction can be evaluated based upon the rate of peroxide conversion and the extent of peroxide selectivity exhibited. In some embodiments, the peroxide conversion is from about 10% to about 99% including from about 40% to about 99%, from about 90% to about 99%, from about 40% to greater than or about 99% and from about 50% to about 99%. In some embodiments, the peroxide conversion is greater than about 10% and the peroxide selectivity is greater than about 40%.

II. Transition Metal Epoxidation Catalysts

The epoxidation reaction may further comprise using a transition metal catalyst which helps to facilitate the reaction and increase the yield of the desired products. In some embodiments, such transition metal catalysts contain a titanium metal or metal ion which forms the reactive species with the alkene or aralkene. In further embodiments, the catalyst is a titanium catalyst wherein the titanium is impregnated on a solid support. A catalyst may contain between 0.01% and 20% by weight of titanium relative to the total weight of the catalyst. In certain embodiments, the catalyst may contain between 0.1% and 10% by weight of titanium relative to the total weight of the catalyst, including between 1% and 6% by weight and between 3% and 5% by weight of titanium relative to the total weight of the catalyst.

In some embodiments, the inert solid support is a silica based zeolite wherein some of the silica atoms in the crystal lattice have been replaced with titanium or another catalytically active metal or metal ion. In further embodiments, the solid support which has been modified with titanium is a zeolite. In additional embodiments, the solid support is a molecular sieve such as a silicalites. In certain embodiments, the solid support has the topology of the ZSM-5 aluminosilicate, the ZSM-11 aluminosilicate, or the MWW aluminosilicate zeolites. Titanium doped zeolites of the MWW family and their synthesis are known, such as those described in U.S. Pat. No. 6,759,540, which is incorporated herein by reference. In some embodiments, the solid support comprises from approximately 80 to 99.99% by weight of the catalyst as a percentage of the total weight of the catalyst, including from 90% to 99.9% by weight, from 94% to 99% by weight and from 95% to 97% by weight of the catalyst as a percentage of the total weight of the catalyst.

In some embodiments, the support is a porous material. Supports which can be used with noble metal and titanium catalysts are known in the relevant art. It is contemplated that any support may be used with the epoxidation catalyst described in the present disclosure. In some non-limiting examples, the support is an inorganic oxide(s), inorganic chloride(s), carbon and organic polymer resin. In some embodiments, the solid support includes oxides of Group 2, 3, 4, 5, 6, 13 or 14 elements. In further embodiments, the solid support is silica, alumina, titania, zirconia, niobium oxides, tantalum oxides, molybdenum oxides, tungsten oxides, amorphous titania-silica, amorphous zirconia-silica, amorphous niobia-silica and similar oxides. In additional embodiments, the organic polymer supports include, but are not limited to, polystyrene, styrene-divinylbenzene copolymers, crosslinked polyethyleneimines and polybenzimidazole. In certain embodiments, the support also includes combinations of organic polymers grafted onto inorganic oxide supported. In some embodiments, the combination supports include polyethyleneimine-silica supports. In further embodiments, the support is carbon. In still further embodiments, the support is a solid support selected from carbon, silica, silica aluminas, titania, zirconia, and niobia.

In some aspects of the present disclosure, the inert solid support is siliceous solid, alumina, inorganic oxides, carbon, or organic polymers. In certain embodiments, the solid support is a siliceous solid including but not limited to synthetic porous silicas, silica powders, refractory oxides, mesoporous molecular sieves, essentially pure silica and other siliceous solids. In further embodiments, the inert solid support is comprised of silicon dioxide ($SiO_2$), such as amorphous forms of silicon dioxide.

In some embodiments, the solid support is synthetic porous silica such as a silica gel or a precipitated silica. In further embodiments, the synthetic porous silica comprises particles of amorphous silica that are flocculated or linked together such that the particles form a relatively dense and close packed core which have numerous pores, voids or interstices that run throughout the structure. In other embodiments, the solid support is a synthetic silica powder. In some embodiments, the synthetic silica powder includes but is not limited to fumed, pyrogenic silicas from the reaction of a silicon halide with hydrogen and oxygen. In further embodiments, the synthetic silica powders comprise particles of amorphous silica into loose, open packed aggregates which are readily disintegrated. In still further embodiments, the solid support is a refractory oxide including but not limited to silica-aluminas, silica-magnesias, silica-zirconias, silica-alumina-borias, silica-alumina-magnesias and similar compounds. In additional embodiments, these oxide compounds contain a significant weight percentage of silica. In other embodiments, the solid support is a molecular sieve including but not limited to such molecular sieves as the MCM-41, MCM-48, M41S, ZSM-5, XSM-11 and MWW class of molecular sieves. In some embodiments, the solid support is pure silica wherein pure silica is defined as being at least 95% silica by weight, including greater than 97% silica and greater than 99% silica. Essentially pure silica can be obtained commercially. In some embodiments, suitable essentially pure silicas include but are not limited to suitable silicas sold by Davisil® silicas such as Davisil® 643 and microspherical silica gels sold by PQ Corporation including MS-3050 silica. In other embodiments, the solid support comprises naturally occurring mineral silicas including but not limited to hydrous magnesium silicates and clay minerals such as hectorites, kaolins and bentonites.

In some embodiments, the inert solids have a surface area from about 10 to about 1500 $m^2/g$. In further embodiments, the inert solid has a surface area from about 50 $m^2/g$ to about 1000 $m^2/g$, such as from about 100 $m^2/g$ to about 800 $m^2/g$. Furthermore, in additional embodiments, the inert solid have a pore volume in the range of 0.5 to 8.0 mL/g, such as from about 0.1 mL/g to about 6.0 mL/g and from 0.5 mL/g to about 5.0 mL/g. While the size of the inert solid particles can vary depending on other reaction conditions, in certain embodiments, the average particle size is from about 0.1 m to about 1.5 cm. Additionally, in some embodiments, the pore diameter of the catalytic material can vary but the average pore size of the inert solid is from 1 to about 1000 Å. In certain embodiments, the average pore size is from about 50 to 500 Å.

In some aspects of the present disclosure, the solid support is a variety of different physical forms including but not limited to powders, flakes, granules, spheres or pellets. In additional embodiments, the solid support originates in one form and be used in that form or the solid support is converted into a different through techniques known to those of skill in the art. Such conventional techniques include but are not limited to extrusion, pelletization and grinding.

In further embodiments, the titanium source for the deposition of the catalytically active titanium atoms is a titanium halide, titanium alkoxide, or titanium esters. In certain embodiments, the titanium source is a titanium halide, titanium alkoxide or a titanium ester in which the titanium metal is in the $4^+$ oxidation state. In further embodiments, the titanium source for incorporation into the inert solid is a titanium tetrahalide and is preferably titanium tetrachloride. In additional embodiments, the titanium tetrachloride is used as a gas or as a part of a solution with an appropriate solvent. Appropriate solvents include hydrocarbon or aromatic solvents. Furthermore, in some embodiments, commercially available solutions of titanium tetrachloride can be used as a source of titanium.

In some aspects of the present disclosure, the inert solid is be calcined before, after or during the incorporation of the titanium. In additional embodiments, the inert solid is calcined at a temperature from about 400° C. to about 1000° C., including from about 400° C. to about 800° C. and from about 600° C. to about 800° C. In certain embodiments, the calcination may take place under an inert atmosphere, such as under helium, argon, neon or nitrogen. In further embodiments, nitrogen comprises the inert atmosphere. In some embodiments, the calination is performed for about 0.1 to about 24 hours, such as for about 1 to 18 hours or for about 1 to 4 hours. In some embodiments, the calcination changes the peroxide conversion percentage or the peroxide selectivity of a given catalyst and in a given catalytic system. In some embodiments, the calination increases the peroxide conversion and the peroxide selectivity of a given reaction.

In some embodiments, the transition metal catalyst comprises an additional metal other than titanium, including but not limited to palladium, platinum, gold or other noble metals.

In some aspects of the present disclosure, the catalyst may be in the form of a powder or as a large particle size solid and may be spray dried, pelletized or extruded prior to use in the epoxidation. If spray dried, pelletized or extruded, the catalyst may comprise a binder or the like and may be molded, spray dried, shaped or extruded into any desired form prior to use in epoxidation. The catalyst might also be encapsulated in polymer as described in U.S. Pat. No. 7,030,255, the teachings of which are incorporated herein by reference in their entirety.

In some aspects of the present disclosure, the epoxidation reaction further comprises a titanium catalyst wherein the titanium is impregnated on a solid support. In some embodiments, the titanium catalyst is TiMWW or a layered TiMWW catalyst wherein the titanium is impregnated in the aluminosilicate MWW zeolite. In some embodiments, the TiMWW catalyst has an XRD spectra as is shown in the FIGURE herein. The method of preparation of a TiMWW catalyst is known to one of skill in the art. In some aspects, the preparation has been taught in, for example, in U.S. Pat. No. 6,759,540, Wu et al. (2001), U.S. Pat. No. 8,124,555 and U.S. Pat. No. 8,440,846, the contents of which are incorporated herein by reference in their entirety. The titanium MWW zeolite catalyst principally comprises titanium, silicon and oxygen but may also comprise boron and/or small amounts of iron, aluminum, sodium, potassium, copper or other similar elements. Post treatment of the TiMWW catalyst with a template yields layered TiMWW-NAW. Washing Ti-MWW-NAW with an acid yields layered TiMWW-AW. The layered TiMWW-NAW can also be prepared via hydrothermal synthesis of silica, tetrabutyl orthotitanate and a template in the presence of crystallization agent, like boric acid. The layered TiMWW-AW can then be obtained by refluxing layered TiMWW-NAW with $HNO_3$ or $H_2SO_4$ solution. Since boron is detrimental to the catalyst activity, the post treatment method for the synthesis of layered TiMWW catalyst is often used because this treatment of the catalyst removes additional boron.

Such titanium MWW zeolite catalysts, referred to herein as "TiMWW catalysts," are known to have the following empirical formula: $xTiO_2.(1-x)SiO_2$, wherein x is a numeral from about 0.0001 and about 0.5. In some embodiments, x is from about 0.01 to about 0.125. In another context, the ratio of Si:Ti in the lattice framework may range from about 9.5:1 to about 99:1, such as from about 9.5:1 to about 60:1. In some applications, titanium rich MWW catalysts are utilized in the present technology.

The epoxidation process described in the present disclosure may use a catalyst which is either a powder or a large particle size solid. In some embodiments of the present process, the zeolite catalyst may be used as a powder but it is also contemplated that the zeolite catalyst can be used if spray dried, pelletized or extruded. Additionally, the zeolite catalyst may further comprise a binder before the catalyst is shaped, spray dried, molded or extruded into a particular desired form. Additionally, the catalyst in some embodiments is either in a suspension or a fixed-bed form.

In another embodiment, a layered TiMWW catalyst is used to epoxide the alkene. The layered TiMWW catalyst may be used with a template to prepare the catalyst. Some templating agents that may be used are piperidine, hexamethyleneimine, adamantyl ammonium hydroxide, octyltrimethylammonium hydroxide, hetyltrimethylammonium hydroxide, hexyltrimethylammonium hydroxide, hexyltrimethylammonium hydroxide or trimethyladamantylammonium hydroxide. In some embodiments, the templating agent is hexamethyleneimine or piperidine. In one embodiment, the templating agent is piperidine. After reaction of the TiMWW catalyst with the templating agent, in some embodiments, the catalyst is washed with an acid. In some aspects, the acids that the catalyst can be washed with include nitric acid, hydrochloric acid, sulfuric acid, sulfurous acid, phosphoric acid or ammonium chloride. In some embodiments, the TiMWW catalyst and the layered TiMWW catalyst have the XRD spectra as is shown the FIGURE.

In some embodiments, the epoxidation catalyst further comprises adding a palladium complex. In some embodiments, the palladium complex allows the reaction of molecular oxygen with an alcohol and the alkene to form the appropriate epoxide. Some non-limiting palladium complexes include those taught by JP Pat. Doc. 2011-111431.

III. Process Scale-Up

The above described methods can be further modified and optimized for preparative, pilot- or large-scale production, either batch or continuous, using the principles and techniques of process chemistry as applied by a person skilled in the art. Such principles and techniques are taught, for example, in *Practical Process Research & Development* (2012), which is incorporated by reference herein.

IV. Definitions

When used in the context of a chemical group, "hydrogen" means —H; "hydroxy" means —OH; "oxo" means =O; "carbonyl" means —C(=O)—; "carboxy" means —C(=O)OH (also written as —COOH or —$CO_2H$); "halo" means independently —F, —Cl, —Br or —I; and "amino" means —$NH_2$. When used in the context of a chemical group, "carboxylate" means a molecule which contains the group —C(=O)O⁻ (also written as C(O)O⁻ or —$CO_2^-$) and the overall charge of the molecule is negative or "halide" means a halogen atom formulated as an anion bearing a single negative charge. Any undefined valency on an atom of a structure shown in this application implicitly represents a hydrogen atom bonded to that atom.

In the context of chemical formulas, the symbol "—" means a single bond, "=" means a double bond, and "≡" means triple bond. The symbol "----" represents an optional bond, which if present is either single or double. The symbol "====" represents a single bond or a double bond. Thus, for example, the formula

includes

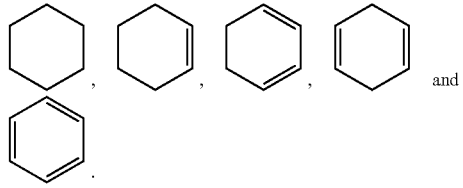

It is understood by the skilled artisan that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "∼∼∼", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◀" means a single bond where the group attached to the thick end of the wedge is "out of the page." The symbol "⦀" means a single bond where the group attached to the thick end of the wedge is "into the page". The symbol "∼∼∼" means a single bond where the geometry around a double bond (e.g., either E or Z) is undefined. Both options, as well as combinations thereof, are therefore intended. The bond orders described above are not limiting when one of the atoms connected by the bond is a metal atom (M). In such cases, it is understood that the actual bonding may comprise significant multiple bonding and/or ionic character. Therefore, unless indicated otherwise, the formulas M-C, M=C, M----C, and M≡≡≡C, each refers to a bond of any type and order between a metal atom and a carbon atom.

For the groups and classes below, the following parenthetical subscripts further define the group/class: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms. (Cn-n') defines both the minimum (n) and maximum number (n') of carbon atoms in the group. Similarly, "alkyl$_{(C2-10)}$" designates those alkyl groups having from 2 to 10 carbon atoms.

The term "saturated" as used herein means the compound or group so modified has no carbon-carbon double bonds and no carbon-carbon triple bonds, except as noted below. In the case of substituted versions of saturated groups, one or more carbon oxygen double bonds or a carbon nitrogen double bond may be present. When such a bond is present, carbon-carbon double bonds that may occur as part of keto-enol tautomerism or imine/enamine tautomerism are not precluded.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl).

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. As used herein, "cycloalkyl" is a subset of alkyl, with the carbon atom that forms the point of attachment also being a member of one or more non-aromatic ring structures, wherein the cycloalkyl group consists of no atoms other than carbon and hydrogen. As used herein, cycloalkyl does not preclude the presence of one or more alkyl groups (carbon number limitation permitting) attached to the ring or ring system. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), —CH$_2$C(CH$_3$)$_3$ (neo-pentyl), cyclobutyl, cyclopentyl, cyclohexyl and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and

are non-limiting examples of alkanediyl groups. It is noted that while the alkenediyl group is aliphatic, once connected at both ends, this group is not precluded from forming an aromatic structure. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include =CH$_2$, =CH(CH$_2$CH$_3$), and =C(CH$_3$)$_2$. An "alkane" refers to the compound H—R, wherein R is alkyl as this term is defined above. When any of these terms is used with the "substituted" modifier one or more hydrogen atoms has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —SiCl$_2$CH$_3$ or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$ and —CH$_2$CH$_2$Cl. The term "haloalkyl" is a subset of substituted alkyl, in which one or more hydrogen atoms has been substituted with a halo group and no other atoms aside from carbon, hydrogen and halogen are present. The group —CH$_2$Cl is a non-limiting example of a haloalkyl. The term "fluoroalkyl" is a subset of substituted alkyl, in which one or more hydrogens has been substituted with a fluoro group and no other atoms aside from carbon, hydrogen and fluorine are present. The groups —CH$_2$F, —CF$_3$, and —CH$_2$CF$_3$ are non-limiting examples of fluoroalkyl groups.

The term "alkenyl" when used without the "substituted" modifier refers to a monovalent unsaturated aliphatic group with a carbon atom as the point of attachment, a linear or branched, cyclo, cyclic or acyclic structure, at least one nonaromatic carbon-carbon double bond, no carbon-carbon triple bonds and no atoms other than carbon and hydrogen. Non-limiting examples of alkenyl groups include —CH=CH$_2$ (vinyl), —CH=CHCH$_3$, —CH=CHCH$_2$CH$_3$, —CH$_2$CH=CH$_2$ (allyl), —CH$_2$CH=CHCH$_3$ and —CH=CHCH=CH$_2$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, —CH=CHCH$_2$—, and

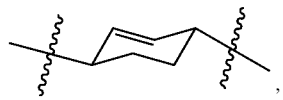 [SMILES: *C1C=CC(*)CC1]

are non-limiting examples of alkenediyl groups. The terms "alkene" or "olefin" are synonymous and refer to a compound having the formula H—R, wherein R is alkenyl as this term is defined above. A "terminal alkene" refers to an alkene having just one carbon-carbon double bond, wherein that bond forms a vinyl group at one end of the molecule. When any of these terms are used with the "substituted" modifier one or more hydrogen atoms has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —SiCl$_2$CH$_3$ or —S(O)$_2$NH$_2$. The groups —CH=CHF, —CH=CHCl and —CH=CHBr are non-limiting examples of substituted alkenyl groups.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s), wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic rings present. If more than one ring is present, the rings may be fused or unfused. Unfused rings may be connected via one or more of the following: a covalent bond, alkanediyl or alkenediyl groups (carbon number limitation permitting). Non-limiting examples of arenediyl groups include:

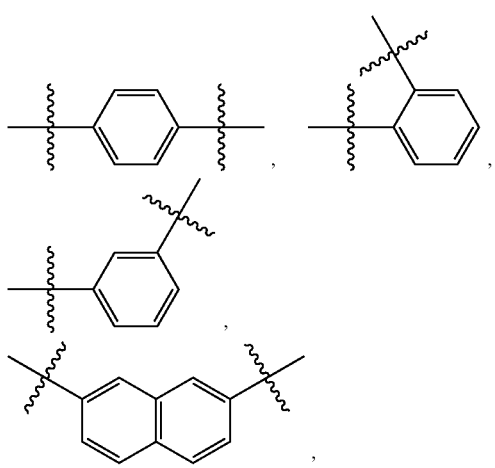

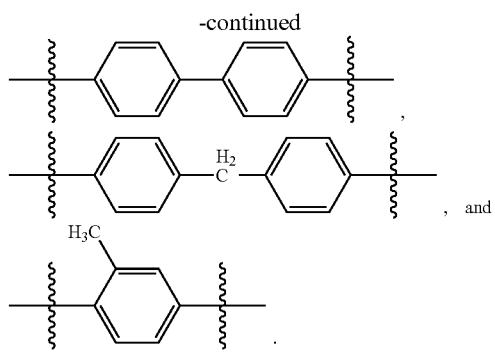

An "arene" refers to the compound H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —SiCl$_2$CH$_3$ or —S(O)$_2$NH$_2$.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —SiCl$_2$CH$_3$ or —S(O)$_2$NH$_2$. Non-limiting examples of substituted aralkyls are (3-chlorophenyl)-methyl and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl and triazolyl. The term "N-heteroaryl" refers to a heteroaryl group with a nitrogen atom as the point of attachment. The term "heteroarenediyl" when used without the "substituted" modifier refers to an divalent aromatic group, with two aromatic carbon atoms, two aromatic nitrogen atoms or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. If more than one ring is present, the rings may be fused or unfused. Unfused rings may be connected via one or more of the following: a covalent bond, alkanediyl or alkenediyl groups (carbon number limitation permitting). As used herein, the term does not preclude the presence of one or more alkyl, aryl, and/or aralkyl groups (carbon number limitation permitting) attached to the aromatic ring or aromatic ring system. Non-limiting examples of heteroarenediyl groups include:

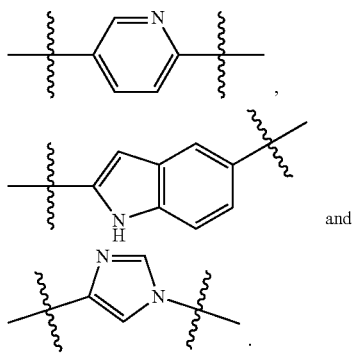

A "heteroarene" refers to the compound H—R, wherein R is heteroaryl. Pyridine and quinoline are non-limiting examples of heteroarenes. A "heteroarenium" is a protonated or N-alkylated nitrogen containing heteroarene as that term is defined above, wherein the nitrogen atom has been protonated or alkylated to have a positive charge. When these terms are used with the "substituted" modifier one or more hydrogen atoms has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$ or —S(O)$_2$NH$_2$.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. If more than one ring is present, the rings may be fused or unfused. As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl and oxetanyl. The term "N-heterocycloalkyl" refers to a heterocycloalkyl group with a nitrogen atom as the point of attachment. The term "heterocycloalkanediyl" when used without the "substituted" modifier refers to a divalent cyclic group, with two carbon atoms, two nitrogen atoms or one carbon atom and one nitrogen atom as the two points of attachment, said atoms forming part of one or more ring structure(s) wherein at least one of the ring atoms is nitrogen, oxygen or sulfur, and wherein the divalent group consists of no atoms other than carbon, hydrogen, nitrogen, oxygen and sulfur. If more than one ring is present, the rings may be fused or unfused. Unfused rings may be connected via one or more of the following: a covalent bond, alkanediyl or alkenediyl groups (carbon number limitation permitting). As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkanediyl groups include:

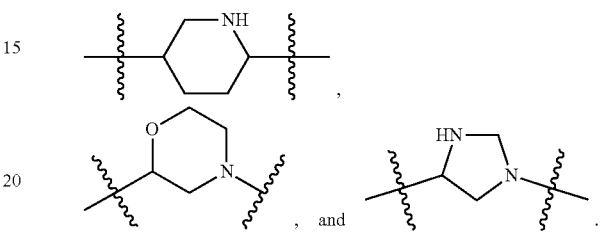

When these terms are used with the "substituted" modifier one or more hydrogen atoms has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —S(O)$_2$NH$_2$, or —C(O)OC (CH$_3$)$_3$ (tert-butyloxycarbonyl, BOC).

The term "acyl" when used without the "substituted" modifier refers to the group —C(O)R, in which R is a hydrogen, alkyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH (CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$ and —C(O)(imidazolyl) are non-limiting examples of acyl groups. The terms "alkylcarboxylate" "alkenylcarboxylate", "alkynylcarboxylate", "arylcarboxylate", "aralkylcarboxylate", "heteroarylcarboxylate" and "heterocycloalkylcarboxylate" when used without the "substituted" modifier, refers to groups, defined as —OC(O)R, in which R is alkyl, alkenyl, alkynyl, aryl, aralkyl, heteroaryl and heterocycloalkyl, respectively. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group. When any of these terms are used with the "substituted" modifier one or more hydrogen atoms (including a hydrogen atom directly attached the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$ or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl) and —CON(CH$_3$)$_2$, are non-limiting examples of substituted acyl groups.

The term "alkylamino" when used without the "substituted" modifier refers to the group —NHR, in which R is an alkyl, as that term is defined above. Non-limiting examples of alkylamino groups include —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH₃)₂, —N(CH₃)(CH₂CH₃) and N-pyrrolidinyl. The terms "alkenylamino", "alkynylamino", "arylamino", "aralkylamino", "heteroarylamino" and "heterocycloalkylamino" when used without the "substituted" modifier, refers to groups, defined as —NHR, in which R is alkoxy, alkenyl, alkynyl, aryl, aralkyl, heteroaryl and heterocycloalkyl, respectively. The term "alkylammonium" when used without the "substituted" modifier refers to the group ⁺NH₃R, in which R is an alkyl, as that term is defined above. Non-limiting examples of alkylammonium groups include ⁺NH₃CH₃ and ⁺NH₂CH₂CH₃. The term "tetraalkylammonium" when used without the "substituted" modifier refers to the group —NRR'R"R"', in which R, R', R" and R"' can be the same or different alkyl groups, or two of R, R', R" and R"' can be taken together to represent an alkanediyl. The terms "alkenylammonium", "alkynylammonium", "arylammonium", "aralkylammonium", "heteroarylammonium" and "heterocycloalkylammonium" when used without the "substituted" modifier, refers to groups, defined as —NHR, in which R is alkenyl, alkynyl, aryl, aralkyl, heteroaryl and heterocycloalkyl, respectively. A non-limiting example of an arylamino group is —NHC₆H₅. The term "amido" (acylamino), when used without the "substituted" modifier, refers to the group —NHR, in which R is acyl, as that term is defined above. A non-limiting example of an amido group is —NHC(O)CH₃. The term "alkylimino" when used without the "substituted" modifier refers to the divalent group =NR, in which R is an alkyl, as that term is defined above. The term "alkylaminodiyl" refers to the divalent group —NH-alkanediyl-, —NH-alkanediyl-NH— or -alkanediyl-NH-alkanediyl-. When any of these terms is used with the "substituted" modifier one or more hydrogen atoms has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃ or —S(O)₂NH₂. The groups —NHC(O)OCH₃ and —NHC(O)NHCH₃ are non-limiting examples of substituted amido groups.

The term "alkoxy" when used without the "substituted" modifier refers to the group —OR, in which R is an alkyl, as that term is defined above. Non-limiting examples of alkoxy groups include —OCH₃ (methoxy), —OCH₂CH₃ (ethoxy), —OCH₂CH₂CH₃, —OCH(CH₃)₂ (isopropoxy) and —OC(CH₃)₃ (tert-butoxy). The terms "alkenyloxy", "aryloxy", "aralkoxy", "heteroaryloxy", "heterocycloalkoxy" and "acyloxy", when used without the "substituted" modifier, refers to groups, defined as —OR, in which R is alkenyl, aryl, aralkyl, heteroaryl, heterocycloalkyl and acyl, respectively. The term "alkoxydiyl" refers to the divalent group —O-alkanediyl-, —O-alkanediyl-O— or -alkanediyl-O-alkanediyl-. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃ or —S(O)₂NH₂.

The use of the word "a" or "an," when used in conjunction with the term "comprising" in the claims and/or the specification may mean "one," but it is also consistent with the meaning of "one or more," "at least one" and "one or more than one."

Throughout this application, the term "about" is used to indicate that a value includes the inherent variation of error for the device, the method being employed to determine the value or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps but also covers other unlisted steps.

The term "epoxide" is a structure with a three-membered ring containing an oxygen atom and two carbon atoms joined by single bonds. An epoxide has the following general formula:

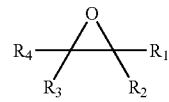

wherein: $R_1$, $R_2$, and $R_3$ are each independently selected from hydrogen, substituted or unsubstituted alkyl and $R_4$ is selected from hydrogen, substituted or unsubstituted alkyl, or substituted or unsubstituted aryl.

A Group 1 atom comprises an atom selected from lithium, sodium, potassium, rubidium, cesium or francium. A Group 2 atom comprises an atom selected from beryllium, magnesium, calcium, strontium, barium or radium. A cation of these atoms results in a positively charged atom which has a +1 charge for Group 1 atoms or a cation of the Group 2 atoms having a +2 charge.

An "isomer" of a first compound is a separate compound in which each molecule contains the same constituent atoms as the first compound, but where the configuration of those atoms in three dimensions differs.

A "method" is series of one or more steps undertaken that leads to a final product, result or outcome. As used herein, the word "method" is used interchangeably with the word "process".

A "peroxide" is a molecule containing a single covalent bond between two oxygen atoms and each oxygen is also bound to a hydrogen, alkyl, alkenyl, alkynyl, aryl, aralkyl, heteroaryl or heterocycloalkyl group as those groups are defined above. In general, the peroxide bond between the two oxygen atoms is labile and readily decomposes or reacts with other molecules, particularly in the presence of a catalyst. Some non-limiting examples of peroxides include HO—OH (hydrogen peroxide) or (CH₃)₃CO—OH (tert-butyl hydroperoxide).

The term "peroxide conversion" when used in the context of this application means the percentage of the peroxide which has been converted into the corresponding alcohol or water byproduct. For example, the peroxide conversion of tert-butyl hydroperoxide is represented by the amount of the starting peroxide which has been converted into tert-butanol in a given epoxidation reaction.

The term "peroxide selectivity" when used in the context of this application means the percentage of the peroxide that has been incorporated into the desired epoxide.

The term "1-phenylethyl alcohol" or "1-phenylethanol" is used interchangeably with the term "α-methyl benzyl alcohol."

The term "silicate" when used in the context of this application indicates an anionic silicon compound. In some embodiments, the silicon is bound to oxygen atoms or halide atoms and the silicon atom has a tetrahedral orientation. In some embodiments, the silicon can adopt a higher coordination number and adopt other orientations such as octahedral. In some embodiments, a silicate exists as a cyclic, straight single chain or sheet forming silicate. In some embodiments, the silicate is an orthosilicate such as "$SiO_4^{4-}$". The term "aluminosilicate" is a compound comprising aluminum, silicon and oxygen with an appropriate counteraction(s). One non-limiting example of an aluminosilicate is kaolin, which has the molecular formula $Al_2Si_2O_5(OH)_4$. In some embodiments, hydrated aluminosilicates are zeolites.

The anions "sulfate", "carboxylates" or "phosphate" when used herein are intended to represent the fully deprotonated as well as the partially and fully protonated forms of these anions. In one non-limiting example, the term sulfate is used to imply $H_2SO_4$, $HSO_4^-$ and $SO_4^{2-}$.

The above definitions supersede any conflicting definitions in any reference that is incorporated by reference herein.

V. Examples

The following examples are included to demonstrate certain embodiments of the subject matter of the appended claims. It should be appreciated by those of skill in the art that the techniques disclosed in the examples which follow represent techniques intended to function well in the practice of the subject matter of the appended claims. However, those of skill in the art should, in light of the present disclosure, appreciate that many changes can be made in the specific embodiments which are disclosed and still obtain a like or similar result without departing from the spirit and scope of the appended claims.

Example 1: Use of Buffers and Large Molecule Solvents in the Epoxidation of Alkenes

TABLE 1

Peroxide Conversion and Selectivity of $H_2O_2$ Utilization

| Sample | Zeolite Catalyst | Solvent | Buffer | Temp (° C.) | $H_2O_2$ conversion (%) | Ring Opening (%) | $H_2O_2$ selectivity to PO (%) |
|---|---|---|---|---|---|---|---|
| 1 | TS-1 | methanol/water | — | 50 | 48 | — | 78 |
| 2 | TS-1 | methanol/water | Ammonium acetate | 50 | 15 | — | 68 |
| 3 | TS-1 | t-butyl alcohol/water | — | 50 | 12 | — | 58 |
| 4 | TS-1 | t-butyl alcohol/water | Ammonium dihydrogen phosphate | 50 | 11 | — | 15 |
| 5 | TS-1 | Acetonitrile/water | — | 50 | 7 | — | 92 |
| 6 | TS-1 | Acetonitrile/water | Ammonium dihydrogen phosphate | 50 | 4 | — | 100 |
| 7 | TiMWW | t-butyl alcohol/water | — | 50 | 43 | 0.6 | 75 |
| 8 | TiMWW | t-butyl alcohol/water | Ammonium dihydrogen phosphate | 50 | 99 | 0.3 | 80 |
| 9 | TiMWW | 1-phenylethyl alcohol/acetophenone | — | 70 | 20.9 | 1.72 | 93 |
| 10 | TiMWW | 1-phenylethyl alcohol/acetophenone | Ammonium acetate | 70 | 99.2 | 0.33 | 99 |
| 11 | TiMWW | 1-phenylethyl alcohol/acetophenone | Ammonium dihydorgen phosphate | 70 | 96.8 | 0.331 | 97 |

As shown in Table 1, the epoxidation catalyst, TS-1, with small molecule solvents such as methanol leads to moderate hydrogen peroxide conversion as can be seen in Sample 1, but that $H_2O_2$ conversion was reduced when TS-1 is used with a buffer (Sample 2 vs. Sample 1). Additionally, other solvents like large molecule solvents, e.g. acetonitrile and t-BuOH, also lead to a reduction of hydrogen peroxide conversion compared to methanol (Samples 3 and 5 vs. Sample 1). Finally, when both the large molecule solvents are used in conjunction with a buffer, the amount of hydrogen peroxide conversion level was further reduced (Samples 4 and 6 vs. Sample 1 and Samples 3 and 5). The epoxidation catalyst, TiMWW, gave a similar hydrogen peroxide conversion to the TS-1 catalyst (Sample 7 vs. Sample 1). Additionally, the use of TiMWW catalyst with 1-phenylethyl alcohol and acetophenone leads to lowered hydrogen peroxide conversion (Sample 9 vs. Sample 1). Moreover, the use of TiMWW catalyst in the presence of a buffer with t-butyl alcohol and water or with 1-phenylethyl alcohol and acetophenone leads to a greatly increased hydrogen peroxide conversion as well as hydrogen peroxide selectivity to propylene oxide and reduced ring opening by-products. (Samples 8, 10, and 11 vs. Samples 7 and 9).

Sample 1:

A 100 mL Parr reactor is charged with a 70:23:7 wt. % solution of methanol/water/30 wt. % hydrogen peroxide (40 g) and TS-1 catalyst (0.03 g). The reactor is sealed and charged with propylene (about 20-23 g). The magnetically stirred reaction mixture is heated at 50° C. for 30 minutes at a reactor pressure about 300 psig (about 2,170 kPa), then cooled to 10° C. The liquid and gas phases are analyzed by gas chromatography. The results are shown in Table 1.

Sample 2:

A 100 mL Parr reactor is charged with a 70:23:7 wt. % solution of methanol/water/30 wt. % hydrogen peroxide (40 g), 0.5 g of 0.1 M ammonium acetate solution and TS-1 catalyst (0.03 g). The reactor is sealed and charged with propylene (about 21 g). The magnetically stirred reaction mixture is heated at 50° C. for 30 minutes at a reactor pressure about 300 psig (about 2,170 kPa), then cooled to 10° C. The liquid and gas phases are analyzed by gas chromatography. The results are shown in Table 1.

Sample 3:

A 100 mL Parr reactor is charged with a 70:23:7 wt. % solution of t-butyl alcohol/water/30 wt. % hydrogen peroxide (40 g) and TS-1 catalyst (0.03 g). The reactor is sealed and charged with propylene (about 25 g). The magnetically stirred reaction mixture is heated at 50° C. for 30 minutes at a reactor pressure about 300 psig (about 2,170 kPa), then cooled to 10° C. The liquid and gas phases are analyzed by gas chromatography. The results are shown in Table 1.

Sample 4:

A 100 mL Parr reactor is charged with a 70:23:7 wt. % solution of t-butyl alcohol/water/30 wt. % hydrogen peroxide (40 g), 0.5 g of 0.1 M ammonium dihydrogen phosphate solution and TS-1 catalyst (0.03 g). The reactor is sealed and charged with propylene (about 22 g). The magnetically stirred reaction mixture is heated at 50° C. for 30 minutes at a reactor pressure about 300 psig (about 2,170 kPa), then cooled to 10° C. The liquid and gas phases are analyzed by gas chromatography. The results are shown in Table 1.

Sample 5:

A 100 mL Parr reactor is charged with a 70:23:7 wt. % solution of acetonitrile/water/30 wt. % hydrogen peroxide (40 g) and TS-1 catalyst (0.03 g). The reactor is sealed and charged with propylene (about 22 g). The magnetically stirred reaction mixture is heated at 50° C. for 30 minutes at a reactor pressure about 300 psig (about 2,170 kPa), then cooled to 10° C. The liquid and gas phases are analyzed by gas chromatography. The results are shown in Table 1.

Sample 6:

A 100 mL Parr reactor is charged with a 70:23:7 wt. % solution of acetonitrile/water/30 wt. % hydrogen peroxide (40 g), 0.5 g of 0.1 M ammonium dihydrogen phosphate solution and TS-1 catalyst (0.03 g). The reactor is sealed and charged with propylene (about 25 g). The magnetically stirred reaction mixture is heated at 50° C. for 30 minutes at a reactor pressure about 300 psig (about 2,170 kPa), then cooled to 10° C. The liquid and gas phases are analyzed by gas chromatography. The results are shown in Table 1.

Sample 7:

A 100 mL Parr reactor is charged with a 70:23:7 wt. % solution of t-butyl alcohol/water/30 wt. % hydrogen peroxide (40 g) and TiMWW catalyst (0.03 g). The reactor is sealed and charged with propylene (about 24 g). The magnetically stirred reaction mixture is heated at 50° C. for 30 minutes at a reactor pressure about 300 psig (about 2,170 kPa), then cooled to 10° C. The liquid and gas phases are analyzed by gas chromatography. The results are shown in Table 1.

Sample 8:

A 100 mL Parr reactor is charged with a 70:23:7 wt. % solution of t-butyl alcohol/water/30 wt. % hydrogen peroxide (40 g), 0.5 g of 0.1 M ammonium dihydrogen phosphate solution and TiMWW catalyst (0.03 g). The reactor is sealed and charged with propylene (about 24 g). The magnetically stirred reaction mixture is heated at 70° C. for 30 minutes at a reactor pressure about 300 psig (about 2,170 kPa), then cooled to 10° C. The liquid and gas phases are analyzed by gas chromatography. The results are shown in Table 1.

Sample 9:

A 100 mL Parr reactor is charged with a 80:12:8 wt. % solution of 1-phenylethyl alcohol/acetophenone/30 wt. % hydrogen peroxide (50 g) and TiMWW catalyst (0.03 g). The reactor is sealed and charged with propylene (about 15 g). The magnetically stirred reaction mixture is heated at 70° C. for 30 minutes at a reactor pressure about 300 psig (about 2,170 kPa), then cooled to 10° C. The liquid and gas phases are analyzed by gas chromatography. The results are shown in Table 1.

Sample 10:

A 100 mL Parr reactor is charged with a 80:12:8 wt. % solution of 1-phenylethyl alcohol/acetophenone/30 wt. % hydrogen peroxide (50 g), 0.2 g of 0.1 M ammonium acetate solution and TiMWW catalyst (0.03 g). The reactor is sealed and charged with propylene (about 15 g). The magnetically stirred reaction mixture is heated at 70° C. for 30 minutes at a reactor pressure about 300 psig (about 2,170 kPa), then cooled to 10° C. The liquid and gas phases are analyzed by gas chromatography. The results are shown in Table 1.

Sample 11:

A 100 mL Parr reactor is charged with a 80:12:8 wt. % solution of 1-phenylethyl alcohol/acetophenone/30 wt. % hydrogen peroxide (50 g), 0.2 g of 0.1 M ammonium acetate solution and TiMWW catalyst (0.03 g). The reactor is sealed and charged with propylene (about 4.5 g). The magnetically stirred reaction mixture is heated at 70° C. for 30 minutes at a reactor pressure about 300 psig (about 2,170 kPa), then cooled to 10° C. The liquid and gas phases are analyzed by gas chromatography. The results are shown in Table 1.

Example 2: Use of TiMWW Catalyst and Layered TiMWW Catalyst with Buffer and Solvent

TABLE 2

Effects of Catalyst and Buffer on Peroxide Conversion

| Samples | Zeolite Catalyst | Solvent | Buffer | Temp (° C.) | Peroxide conversion (%) |
|---|---|---|---|---|---|
| 12 | TiMWW | t-butyl alcohol/water | — | 70 | 27 |
| 13 | Layered TiMWW-NAW | t-butyl alcohol/water | — | 70 | 99 |
| 14 | Layered TiMWW-AW | t-butyl alcohol/water | — | 70 | 99 |
| 15 | Layered TiMWW-AW | t-butyl alcohol/water | Ammonium Acetate | 70 | 99 |

TABLE 2-continued

Effects of Catalyst and Buffer on Peroxide Conversion

| Samples | Zeolite Catalyst | Solvent | Buffer | Temp (° C.) | Peroxide conversion (%) |
|---|---|---|---|---|---|
| 9 | TiMWW | 1-phenylethyl alcohol/ acetophenone | — | 70 | 20.7 |
| 16 | Layered TiMWW-NAW | 1-phenylethyl alcohol/ acetophenone | — | 70 | 99 |
| 17 | Layered TiMWW-AW | 1-phenylethyl alcohol/ acetophenone | — | 70 | 99 |

Preparation of Layered TiMWW-NAW:

A sealed 100 mL Parr reactor containing 6.1 g of TiMWW, 15 g of piperidine, and 35 g of deionized water is heated at 155° C. for 3 days. The reaction mixture is then cooled, filtered, washed with de-ionized water (6×200 mL) and dried in a vacuum oven at 130° C. for 16 hrs to yield an off-white solid (5.4 g)

Preparation of Layered TiMWW-AW:

A mixture of the layered TiMWW-NAW catalyst (1.5 g) above in 75 mL of 2 M nitric acid is refluxed at 110° C. After 3 hrs, the reaction mixture is then cooled, filtered, washed with de-ionized water (6×200 mL), and dried in a vacuum oven at 130° C. for 16 hrs to yield a white solid (1.2 g).

Sample 12:

A 100 mL Parr reactor is charged with a 70:23:7 wt. % solution of t-butyl alcohol/water/30 wt. % hydrogen peroxide (50 g) and TiMWW catalyst (0.03 g). The reactor is sealed and charged with propylene (about 15 g). The magnetically stirred reaction mixture is heated at 70° C. for 30 minutes at a reactor pressure about 300 psig (about 2,170 kPa), then cooled to 10° C. The liquid and gas phases are analyzed by gas chromatography. The results are shown in Table 3.

Sample 13:

A 100 mL Parr reactor is charged with a 70:23:7 wt. % solution of t-butyl alcohol/water/30 wt. % hydrogen peroxide (50 g) and layered TiMWW-NAW catalyst (0.03 g). The reactor is sealed and charged with propylene (about 15 g). The magnetically stirred reaction mixture is heated at 70° C. for 30 minutes at a reactor pressure about 300 psig (about 2,170 kPa), then cooled to 10° C. The liquid and gas phases are analyzed by gas chromatography. The results are shown in Table 3.

Sample 14:

A 100 mL Parr reactor is charged with a 70:23:7 wt. % solution of t-butyl alcohol/water/30 wt. % hydrogen peroxide (50 g) and layered TiMWW-AW catalyst (0.03 g). The reactor is sealed and charged with propylene (about 15 g). The magnetically stirred reaction mixture is heated at 70° C. for 30 minutes at a reactor pressure about 300 psig (about 2,170 kPa), then cooled to 10° C. The liquid and gas phases are analyzed by gas chromatography. The results are shown in Table 3.

Sample 15:

A 100 mL Parr reactor is charged with a 70:23:7 wt. % solution of t-butyl alcohol/water/30 wt. % hydrogen peroxide (50 g), 0.2 g of 0.1M ammonium acetate and layered TiMWW-AW catalyst (0.03 g). The reactor is sealed and charged with propylene (about 15 g). The magnetically stirred reaction mixture is heated at 70° C. for 30 minutes at a reactor pressure about 300 psig (about 2,170 kPa), then cooled to 10° C. The liquid and gas phases are analyzed by gas chromatography. The results are shown in Table 3.

Sample 16:

A 100 mL Parr reactor is charged with a 80:12:8 wt. % solution of 1-phenylethyl alcohol/acetophenone/30 wt. % hydrogen peroxide (50 g) and layered TiMWW-NAW catalyst (0.03 g). The reactor is sealed and charged with propylene (about 15 g). The magnetically stirred reaction mixture is heated at 70° C. for 30 minutes at a reactor pressure about 300 psig (about 2,170 kPa), then cooled to 10° C. The liquid and gas phases are analyzed by gas chromatography. The results are shown in Table 3.

Sample 17:

A 100-mL Parr reactor is charged with a 80:12:8 wt. % solution of 1-phenylethyl alcohol/acetophenone/30 wt. % hydrogen peroxide (50 g) and layered TiMWW-AW catalyst (0.03 g). The reactor is sealed and charged with propylene (about 15 g). The magnetically stirred reaction mixture is heated at 70° C. for 30 minutes at a reactor pressure about 300 psig (about 2,170 kPa), then cooled to 10° C. The liquid and gas phases are analyzed by gas chromatography. The results are shown in Table 3.

The TiMWW catalyst has been shown to produce moderate peroxide conversion in t-butyl alcohol and lower peroxide conversion in 1-phenylethyl alcohol (Samples 12 and Samples 9, respectively). The use of a layered TiMWW catalyst as described herein gave increased peroxide conversion in t-butyl alcohol/water (Samples 13 and 14 versus Sample 12) or in 1-phenylethyl alcohol/acetophenone (Samples 16 and 17 versus Sample 9). Similarly, the layered TiMWW catalyst when used in conjunction with a buffer also leads to excellent peroxide conversion (See Sample 15).

All of the compounds, complexes, and methods disclosed and claimed herein can be made and executed without undue experimentation in light of the present disclosure. While the compounds, complexes, and methods, as provided herein, have been described in terms of certain embodiments, it will be apparent to those of skill in the art that variations may be applied to the compounds, complexes, and methods, as well as in the steps or in the sequence of steps of the methods described herein without departing from the concept, spirit, and scope of the appended claims. More specifically, it will be apparent that certain agents which are chemically related may be substituted for the agents described herein while the same or similar results would be achieved. All such similar substitutes and modifications apparent to those skilled in the art are deemed to be within the spirit, scope and concept of the technology as defined by the appended claims.

REFERENCES

The following references to the extent that they provide exemplary procedural or other details supplementary to those set forth herein, are specifically incorporated herein by reference.

U.S. Pat. No. 3,351,635
U.S. Pat. No. 4,367,342
U.S. Pat. No. 4,833,260
U.S. Pat. No. 6,759,540
U.S. Pat. No. 7,030,255
U.S. Pat. No. 8,124,555
U.S. Pat. No. 8,440,846
Japanese Publication No. 2004-352771
Japanese Publication No. 2011-111431
Anderson, N. G., Practical Process Research & Development—A Guide For Organic Chemists, 2nd ed., Academic Press, New York, 2012.

March's Advanced Organic Chemistry: Reactions, Mechanisms, and Structure, 2007.

What is claimed is:

1. A method for producing propylene oxide comprising contacting propylene with a titanium silica zeolite catalyst, hydrogen peroxide, an ammonium buffer selected from the group consisting of ammonium acetate and ammonium dihydrogen phosphate, and an $R_1$—OH solvent in a reaction mixture, wherein $R_1$ is a substituted or a unsubstituted alkyl$_{(C \leq 12)}$, aryl$_{(C \leq 12)}$, or aralkyl$_{(C \leq 12)}$, and the peroxide selectivity rate is greater than about 40%.

2. The method of claim 1, wherein the $R_1$—OH solvent further comprises from about 0.1-50% by weight of water.

3. The method of claim 1, wherein the reaction mixture comprising an $R_1$—OH solvent further comprises a second organic solvent selected from:

$$R_1\text{—OH} \quad (I),$$

$$R_2\text{—CN} \quad (II),$$

$$R_3\text{—C(O)—}R_4 \quad (III), \text{ or}$$

$$R_5\text{—O—}R_6 \quad (IV)$$

wherein:
$R_1$ is alkyl$_{(C \leq 12)}$, aryl$_{(C \leq 12)}$, aralkyl$_{(C \leq 12)}$, or a substituted version of any of these groups;
$R_2$ is alkyl$_{(C \leq 12)}$, aryl$_{(C \leq 12)}$, aralkyl$_{(C \leq 12)}$, or a substituted version of any of these groups;
$R_3$ is hydrogen, alkyl$_{(C \leq 6)}$, or substituted alkyl$_{(C \leq 6)}$; and
$R_4$, $R_5$, and $R_6$ are each independently selected from alkyl$_{(C \leq 12)}$, aryl$_{(C \leq 12)}$, aralkyl$_{(C \leq 12)}$, or a substituted version of any of these groups, or are taken together are alkoxydiyl$_{(C \leq 12)}$, alkanediyl$_{(C \leq 12)}$, substituted alkoxydiyl$_{(C \leq 12)}$, or substituted alkanediyl$_{(C \leq 12)}$.

4. The method of claim 3, wherein the $R_1$—OH solvent is 1-phenylethyl alcohol and the second organic solvent is acetophenone, and the reaction mixture comprises a ratio of acetophenone to 1-phenylethyl alcohol of 1:99 to 50:50.

5. The method of claim 1, wherein the titanium silica catalyst comprises a silica zeolite catalyst which comprises a silica framework in which silicon atoms in the silica framework have been replaced with titanium atoms and the zeolite is an aluminosilicate MWW zeolite.

6. The method of claim 1, wherein the ratio of titanium to silica in the titanium silica catalyst comprises a ratio of 0.5 to 5 titanium atoms for every 100 silicon atoms.

7. The method of claim 5, further comprising washing the titanium silica catalyst with a templating agent.

8. The method of claim 7, wherein the templating agent is piperidine, hexamethyleneimine, adamantyl ammonium hydroxide, octyltrimethylammonium hydroxide, hetyltrimethylammonium hydroxide, hexyltrimethylammonium hydroxide, hexyltrimethylammonium hydroxide or trimethyladamantylammonium hydroxide.

9. The method of claim 7, further comprising washing the catalyst with an acid after washing with a templating agent.

10. The method of claim 9, wherein the acid is nitric acid, hydrochloric acid, sulfuric acid, sulfurous acid, phosphoric acid or ammonium chloride.

11. The method of claim 1, wherein the method comprises heating the reaction mixture to a temperature between 20° C. and 250° C.

12. The method of claim 1, wherein the method further comprises reacting the alkene$_{(C \leq 12)}$ or aralkene$_{(C \leq 12)}$ with the titanium silica catalyst for a time period between 1 minute and 6 hours.

13. The method of claim 1, wherein the method further comprises a pressure from 10 psig to 1000 psig.

14. The method of claim 1, wherein the titanium silica zeolite catalyst comprises a ratio of 0.5-14 titanium atoms for every 100 silicon atoms.

* * * * *

UNITED STATES PATENT AND TRADEMARK OFFICE
CERTIFICATE OF CORRECTION

PATENT NO. : 9,932,318 B2
APPLICATION NO. : 15/093270
DATED : April 3, 2018
INVENTOR(S) : Dang et al.

Page 1 of 1

It is certified that error appears in the above-identified patent and that said Letters Patent is hereby corrected as shown below:

In the Specification

In Column 11, Line 65, delete "m" and insert -- µm --

In Column 12, Line 35, delete "calination" and insert -- calcination --

In Column 12, Line 40, delete "calination" and insert -- calcination --

Signed and Sealed this
First Day of February, 2022

Drew Hirshfeld
*Performing the Functions and Duties of the*
*Under Secretary of Commerce for Intellectual Property and*
*Director of the United States Patent and Trademark Office*